United States Patent [19]
Ferguson

[11] Patent Number: 5,065,771
[45] Date of Patent: * Nov. 19, 1991

[54] PROPHYLACTIC/CONTRACEPTIVE DEVICE

[76] Inventor: Jo A. Ferguson, 9014 Ilona, Houston, Tex. 77025

[ * ] Notice: The portion of the term of this patent subsequent to Jan. 19, 2007 has been disclaimed.

[21] Appl. No.: 70,053
[22] Filed: Jul. 6, 1987
[51] Int. Cl.⁵ .............................................. A61F 5/46
[52] U.S. Cl. ................................................ 128/835
[58] Field of Search ....... 128/132 R, 138 R, 127–131, 128/834, 835; 604/330, 327, 331, 349–353, 328

[56] References Cited
U.S. PATENT DOCUMENTS

| D. 32,566 | 4/1900 | Gagnier | 128/834 |
| 760,823 | 5/1904 | Torrence | 128/128 |
| 3,130,721 | 4/1964 | Young | 128/127 |
| 4,496,355 | 1/1985 | Hall et al. | 604/327 |
| 4,664,104 | 5/1987 | Jaicks | 604/353 |

Primary Examiner—C. Fred Rosenbaum
Assistant Examiner—J. L. Kruter
Attorney, Agent, or Firm—Edmund F. Bard

[57] ABSTRACT

An improved prophylactic/contraceptive device is provided for preventing conception and for protecting the vaginal cavity and passage against venereal infection. In particular, the device is preferably composed of a flexible pouch-like member having cap-like portion end fittable over the entrance to the cervix. In addition, detachable tie means and the like are preferably included for anchoring the opposite open end of the pouch-like member to the body and thereby preventing dislocation of the device because of thrusting movement within the vaginal passage.

4 Claims, 1 Drawing Sheet

PROPHYLACTIC/CONTRACEPTIVE DEVICE

BACKGROUND

This invention relates to improved prophylactic and contraceptive methods and apparatus, and more particularly relates to a condom-like device designed for females.

It is well-known that many devices and techniques have been proposed and used to prevent conception and/or venereal disease. Although most such devices and techniques are regarded as generally effective for their intended purpose, they are also commonly regarded as having one or more disadvantages which tend to inhibit their usage.

In particular, the so-called condom is commonly believed to give almost completely reliable protection against both conception and venereal disease. However, most sheath-type condoms and the like are also commonly regarded as an inconvenience, and also as a limitation on the degree of tactile stimulus being sought by the user.

The so-called diaphragm or cervical cap is a device which is also commonly believed to provide almost equally effective protection against conception without the accompanying disadvantage of limiting the degree of tactile stimulus of either partner. However, the diaphragm is also considered an inconvenience at best and, depending upon its particular type and design, is regarded by many users as requiring expertise to achieve both installation and removal. Another disadvantage is that the effectiveness of a diaphragm in preventing conception is also widely believed to depend on its being accurately sized within close dimensional tolerances. Furthermore, the diaphragm is effective only insofar as contraception is concerned.

Some of the foregoing disadvantages are a matter of perception only, and may eventually be largely dispelled by increasingly widespread dissemination of more accurate information regarding the use and function of such devices. Other such disadvantages as those hereinbefore mentioned, however, are clearly based on reality, and it is these real disadvantages which will tend to retard and discourage their usage irrespective of the extent to which increased education may dispel reluctance because of perceived but unreal limitations and disadvantages.

As an example of those perceived disadvantages having insufficient basis in fact, it is now established that installation and removal of most types of diaphragms does not require any special expertise or training. Instead, it is now well known and increasingly accepted that the technique of installing and removing most types of diaphragms can be readily and easily acquired by almost any user with only a minimum of instruction and experimentation. As to the need to size a diaphragm within precise dimensional limits, it is now known that the cervix tends to expand and contract within relatively broad dimensional limits, and that a cervical cap which has been precisely fitted in a clinic or the like will therefore almost certainly be improperly sized to the wearer at a later time when the device is expected to perform its intended function.

In other words, a cervical cap is preferably sized to accommodate expansion of the cervix in response to stimulation of the user. Therefore, the need to conform to precise dimensional limits at the time of fitting is not merely unnecessary but may, of itself, cause discomfort and therefore diminution of satisfaction with the device at the very time when it is intended to perform its intended function. Finally, there can be no serious dispute that, irrespective of what other benefits which may be gained from a diaphragm or cervical cap, such a device affords substantially no protection whatsoever as to venereal or other related communicable disease.

On the other hand, it is beyond serious dispute that a condom which is designed to be worn only at the time of entry is a real inconvenience to the user. Similarly, a sheath-type condom which is designed to fit relatively snugly in order to provide maximum protection, also clearly limits the tactile stimulation desired by the user and therefore constitutes a very real inhibition to the purposes of the wearer.

These and other disadvantages of the various types of prophylactics and contraceptive devices of the prior art are overcome or substantially reduced with the present invention, however, and improved prophylactic and contraceptive methods and devices are herewith provided which can be conveniently employed without the need for special skills or instruction, and which afford reliable and complete protection against both conception and venereal disease without significant limitation as to tactile stimulus and the like.

SUMMARY OF INVENTION

In a preferred embodiment of the present invention, an improved prophylactic/contraceptive device is provided which is basically constructed in the manner of a pouch formed of an extremely thin and flexible material impervious to liquids, and which has its closed end portion formed in the manner of a cervical cap and the like. More particularly, the prophylactic device embodying the concept of the present invention is preferably designed to be inserted into and along the length of vaginal passage with its cap-like end portion fitted onto and over the cervix in a conventional manner. The opposite open end of the device is preferably formed and adapted to extend outwardly of the vaginal passage, and may also extend at least partially outwardly over the adjacent labial surfaces, whereby maximum protection is afforded without impeding either thrusting entry into the vaginal passage or tactile stimulatus of the clitoris or adjacent surfaces of the body. In addition, it is also desirable that the device not extend to or over the entrance to the urinary canal or tract.

An inherent disadvantage in most of the contraceptive or prophylactic devices of the prior art is that they are all regarded as undesirably inconvenient to install and wear at any time except when protection is considered an immediate necessity, and that they are further regarded as an inconvenience at that particular time. In the present invention, the cervical cap portion of the pouch is not intended to afford any protection as such, but is merely designed and intended to secure the device in its intended position notwithstanding movement of the wearer. Accordingly, the cervical cap portion of the pouch is not required to be sized to the same dimensional precision considered necessary for diaphragms of conventional design and purpose. Instead, the cervical cap portion of the present invention is only required to be sized whereby it will merely secure the pouch-like member portion of the device in its intended position within the vaginal passage during and after the device performs its intended function.

Accordingly, it is an object of the present invention to provide an improved prophylactic/contraceptive device and the like which is convenient and simple to install and remove and which does not inhibit or prevent other normal functions.

It is further an object of the present invention to provide improved prophylactic/contraceptive device which permits full and normal tactile stimulation.

It is a particular object of the present invention to provide an improved prophylactic/contraceptive device, comprising an open-ended pouch-like member removably insertable into and along a vaginal passage and and having a cervical cap-like portion for releasably engaging the entry portion of the cervix and further adapted to extend to and partially over the labial surfaces adjacent the entrance to said vaginal passage, and fastening means interconnected with said pouch-like member for releasably securing said pouch-like member in the vaginal passage.

These and other objects and features of the present invention will become apparent from the following detailed description, wherein reference is made to the figures in the accompanying drawings.

IN THE DRAWINGS

DETAILED DESCRIPTION

Figure 1:
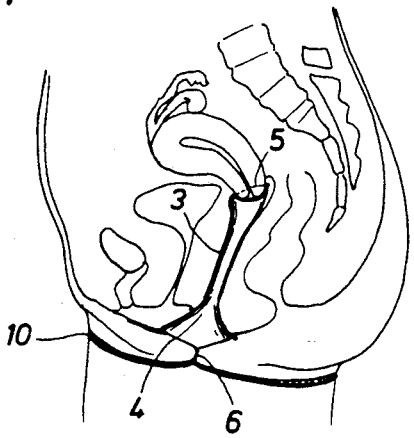
FIG. 1 is a simplified pictorial representation, partly in cross section, of an exemplary embodiment of the present invention, together with a simplified anatomical illustration of its preferred manner of usage for its intended purpose.
Figure 2:
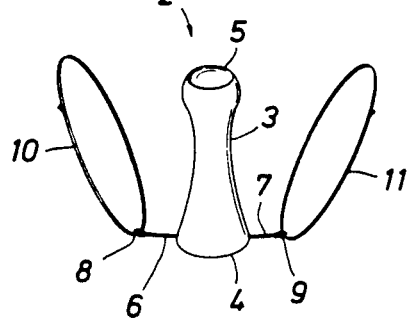
FIG. 2 is a simplified pictorial representation of the essential components of the device illustrated in FIG. 1.

Referring now to FIGS. 1 and 2, there may be seen a simplified pictorial representation of a device 2 embodying the concept and principles of the present invention and adapted to be inserted and maintained in the vaginal passage or cavity for prophylactic and contraceptive purposes as hereinbefore described and explained. More particularly, the device 2 may be seen to be composed of a very thin-walled pouch or sac 3 having a flared open end 4 with a pair of strings 6 and 7 attached at the edge thereof, and having an opposite diaphram-like end portion 5 adapted to engage and close the entrance to the uterine cavity as illustrated in FIG. 1 of the drawing.

Referring again to FIGS. 1 and 2, it may be also seen that the device 2 is preferably provided with a pair of loops 10 and 11, which may conveniently be detachably connected to strings 6 and 7 by suitable fasteners 8 and 9, and which are designed to fit about the legs of the user of the device 2 as illustrated in FIG. 1 of the drawing. As hereinbefore explained, the flared open end 4 of the sac 3 is intended to extend outwardly of and over the labial surfaces of the entry to the vaginal passage or cavity, in order to protect these areas of the body from infection, and also to prevent dislodgement and dislocation of the device 2 during thrusting entry into the vaginal passage and more particularly the device 2 itself. The purpose of the loops 10 and 11 and strings 6 and 7 is to maintain the flared-open configuration of the open end 4 of the sac to achieve this objective, and especially if the device is intended to be installed and maintained in the depicted position for any extended period of time prior to being required to perform its intended function. Accordingly, the loops 10 and 11 are preferably fashioned from any suitable elastic material whereby they may, if desired, be drawn up over or about the hips of the user, and they are further preferably provided with either a thin or flat configuration whereby they will not be visible through the clothes of the user.

As hereinbefore indicated, the outer ends of the strings 6 and 7 may be detachably joined to the elastic loops 10 and 11, by means of fasteners 8 and 9 which may be of any suitable design or type, or the strings 6 and 7 may alternatively be fixedly secured directly to the elastic leg loops 10 and 11. The strings 6 and 7 may also be elastic in character to permit the device 2 to be produced in standard dimensions for use by wearers of various sizes and shapes. As will be further explained in detail, however, the sac 3 is intentionally fabricated with an overall length substantially greater than the length of any vaginal passage, and therefore physical size differences among wearers will be most effectively accommodated by elongation of the sac 3 within the vaginal passage.

Figure 5:
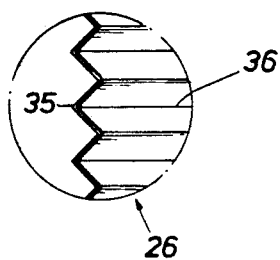
FIG. 5 is a more detailed pictorial representation of a portion of the device illustrated in FIGS. 3 and 4.
Figure 3:
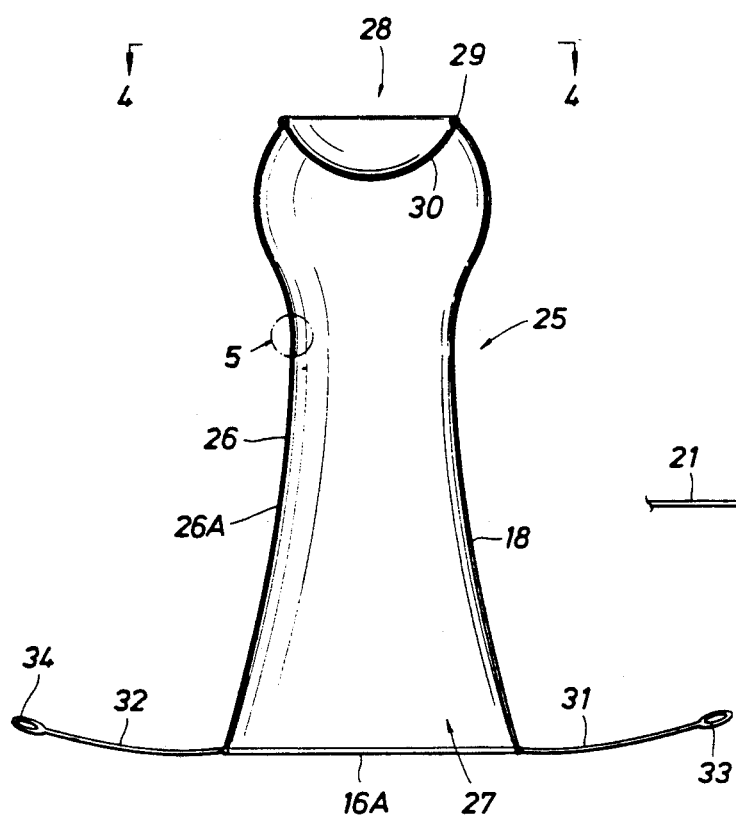
FIG. 3 is a simplified pictorial representation of an alternative embodiment of the present invention.
Figure 4:
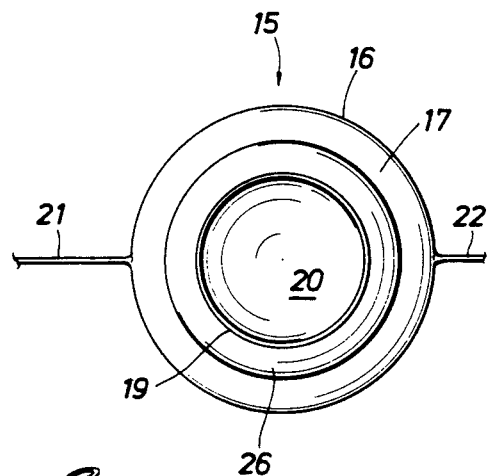
FIG. 4 is another different view of the device illustrated in FIG. 3.

Referring now to FIGS. 3-5 of the accompanying drawing, there may be seen a simplified pictorial representation of a device 25, which is a different alternative form of the invention embodied in device 2. More particularly, and as indicated in FIG. 5, the sidewall 26A of the sac 26 may be formed of a similarly thin but finely corrugated material to more effectively permit the device 25 to be installed and maintained in vaginal passages of various lengths and dimensions. In addition, strings 31 and 32, which are affixed to the outer edge 16A of the open end 17 of the device 25, may be provided with eye-type links 33 and 34 instead of elastic loops as hereinbefore described with respect to device 2. More particularly, these links 33 and 34 may permit engagement with another different means of suspension such as an elastic waist strap (not depicted) and the like in order to provide anchorage for the open end 17 of the device 25 without the discomfort which may be experienced because of the loops 10 and 11.

Referring again to FIGS. 3-5, it will be seen that in other respects the device 25 will preferably be fashioned to perform the same as the device 2 heretofore described. The outer circumferential portion 17 of the open 16 will extend outwardly of and over the labial open portions of the entry to the vaginal passage, but will preferably not extend to or over either the clitoris or the entrance to the urinary canal of the user.

As hereinbefore also stated, the device 25 is preferably provided at its opposite closed end with a portion shaped in the manner of a conventional diaphragm-like end 28. In particular, the diaphragm end 28 is provided with an annular rib-like portion 19 adapted to fit around the entrance of the uterus as illustrated in FIG. 1 of the accompanying drawing, while the concave cap-like portion 20 effectively fits over the entrance to the uterus. The purpose of the cap-like portion 20 is not to close the uterine passage, of course, but to close the sac 26 while at the same time permitting the rib 19 to moor the device within the vaginal passage. Accordingly, the rib 19 and cap 20 need not be sized with the same degree of precision required for conventional diaphragms.

It will be apparent from a consideration of the foregoing explanations and the various structures depicted in the figures in the accompanying drawing, that various other adaptations and modifications may be made without substantial departure from the concept of the present invention. Accordingly, it should be understood that the structures and techniques hereinbefore described are intended as examples only, and are not intended as limitations on the scope of the subject invention.

What is claimed is:

1. An improved prophylactic/contraceptive device, comprising an open-ended pouch-like member removably insertable into and along a vaginal passage in a female body and having a flexible cap-like portion for releasably engaging and closing the entry portion of the cervix therein, said pouch-like member further being formed of a thin flexible material impermeable to human body liquids and forming means to extend within a vaginal passage partially engaged over the labial surfaces adjacent the vaginal orifice, and fastening means releasably attached to the exterior of said female body and flexibly interconnected with said pouch-like member adjacent said entrance to said vaginal passage for releasably securing said pouch-like member in said vaginal passage and partially covering the labial surfaces thereof, said fastening means further including a pair of flexible tie members each having one end connected with said pouch-like member for extending said open-ended portion of said pouch-like member outwardly of said vaginal passage and away from the urinary tract in said female body.

2. The fastening means described in in claim 1, wherein said fastening means further includes anchoring means detachably interconnectable with said tie members and detachably anchorable to the exterior of said female body for drawing the open-ended portion of said pouch-like member partially over said labial portions of said vaginal passage and toward but not over the clitoris of said female body.

3. The anchoring means described in claim 2, further comprising first flexible and elastic loop means interconnected with one of said tie member and adapted to fit about one leg and hip portion of said female body, and second flexible and elastic loop means interconnected with the other of said tie member and adapted to fit about the other leg and hip portion of said female body.

4. The prophylactic/contraceptive device described in claim 2 wherein said tie members each further include link means detachably interconnectable adjacent the waist of said female body.

* * * * *